United States Patent [19]

Malech

[11] Patent Number: 6,060,317

[45] Date of Patent: May 9, 2000

[54] METHOD OF TRANSDUCING MAMMALIAN CELLS, AND PRODUCTS RELATED THERETO

[75] Inventor: Harry L. Malech, Bethesda, Md.

[73] Assignee: The United States of America as represented by the Department of Health and Human Services, Washington, D.C.

[21] Appl. No.: 09/133,033

[22] Filed: Aug. 11, 1998

[51] Int. Cl.[7] .......................... C12N 15/63; C07K 14/78; C12M 1/24

[52] U.S. Cl. ...................... 435/456; 435/320.1; 435/325; 435/304.1; 530/350

[58] Field of Search ................................ 435/456, 320.1, 435/325, 304.1; 530/350

[56] References Cited

U.S. PATENT DOCUMENTS

| | | | |
|---|---|---|---|
| 4,939,151 | 7/1990 | Bacehowski et al. | 435/284 |
| 5,198,423 | 3/1993 | Taguchi et al. | 514/12 |
| 5,302,701 | 4/1994 | Hashi et al. | 530/399 |
| 5,459,069 | 10/1995 | Palsson et al. | 435/289.1 |
| 5,686,278 | 11/1997 | Williams et al. | 435/172.3 |

FOREIGN PATENT DOCUMENTS

| | | |
|---|---|---|
| 0 725 134 A2 | 8/1996 | European Pat. Off. |
| 0 795 606 A1 | 9/1997 | European Pat. Off. |
| 95/26200 | 10/1995 | WIPO |
| 96/13573 | 5/1996 | WIPO |
| 97/11604 | 4/1997 | WIPO |

OTHER PUBLICATIONS

Bergelson et al., "Isolation of a Common Receptor for Coxsackie B Viruses and Adenoviruses 2 and 5," *Science*, 275:1320–1323 (1997).

Chien et al., "The Amphotropic Murine Leukemia Virus Receptor Gene Encodes a 71–Kilodalton Protein That Is Induced by Phosphate Depletion," *J. Virology*, 71:4564–4570 (1997).

Davis et al., "Retroviral Particles Produced from a Stable Human–Derived Packaging Cell Line Transduce Target Cells with Very High Efficiencies," *Hum. Gene Therapy*, 8:1459–1467 (1997).

Dutt et al., "A Recombinant Human Fibronectin Fragment Facilitates Retroviral Mediated Gene Transfer into Human Hematopoietic Progenitor Cells," *Biochem. and Molecular Biol. Int'l.*, 42:909–917 (1997).

Graf et al., "Identification of an Amino Acid Sequence in Laminin Mediating Cell Attachment, Chemotaxis, and Receptor Binding," *Cell*, 48:989–996 (1987).

Hanenberg et al., "Colocalization of retrovirus and target cells on specific fibronectin fragments increases genetic transduction of mammalian cells," *Nature Medicine*, 2:876–882 (1996).

Hanenberg et al., "Optimization of Fibronectin–Assisted Retroviral Gene Transfer into Human CD34[+] Hematopoietic Cells," *Hum. Gene Therapy*, 8:2193–2206 (1997).

Hocking et al., "Activation of Distinct $\alpha_5\beta_1$–mediated Signaling Pathways by Fibronectin's Cell Adhesion and Matrix Assembly Domains," *J. of Cell Biol.*, 141:241–253 (1998).

Huber et al., "Effects of retroviral–mediated tissue plasminogen activator gene transfer and expression on adherence and proliferation of canine endothelial cells seeded onto expanded polytetrafluoroethylene," *J. of Vascular Surgery*, 22:795–803 (1995).

Incardona et al., "Heparin–Binding Domain, Type 1 and Type 2 Repeats of Thrombospondin Mediate Its Interaction With Human Breast Cancer Cells," *J. Cell. Biochem.*, 62:431–442 (1996).

Kimizuka et al., "Production and Characterization of Functional Domains of Human Fibronectin Expressed in *Escherichia coli*," *J.Biochem*, 110:284–291 (1991).

Kornblihtt et al., "Primary structure of human fibronectin: differential splicing may generate at least 10 polypeptides from a single gene," *The EMBO J.*, 4:1755–1759(1985).

Malech et al., "Prolonged production of NADPH oxidase–corrected granulocytes after gene therapy of chronic granulomatous disease," *Proc.Natl.Acad.Sci. USA*, 94:12133–12138(1997).

Malech, Henry L., "Gene Therapy Approach for Chronic Granulomatous Disease," IND Clinical Trial Protocol#9802–231, pp. 1–33, Feb. 11, 1998.

McCann et al., "A Collagen Peptide Motif Activates Tyrosine Kinase–dependent Calcium Signaling Pathways in Human Osteoblast–like Cells," *Matrix Biol.*, 16:273–283 (1997).

Moritz et al., "Bone Marrow Extracellular Matrix Molecules Improve Gene Transfer into Human Hematopoietic Cells via Retroviral Vectors," *J. Clin. Invest.*, 93:1451–1457(1994).

Moritz et al., "Fibronectin Improves Transduction of Reconstituting Hematopoietic Stem Cells by Retroviral Vectors: Evidence of Direct Viral Binding to Chymotryptic Carboxy––Terminal Fragments," *Blood*, 88:855–862(1996).

Pollok et al., "High–Efficiency Gene Transfer into Normal and Adenosine Deaminase–Deficient T Lymphocytes Is Mediated by Transduction on Recombinant Fibronectin Fragments," *J. of Virology*, 72:4882–4892(1998).

Robinet et al., "A Closed Culture System for the Ex Vivo Transduction and Expansion of Human T Lymphocytes," *J. Hematotherapy*, 7:205–215 (1998).

(List continued on next page.)

*Primary Examiner*—John S. Brusca
*Attorney, Agent, or Firm*—Campbell & Flores LLP

[57] ABSTRACT

In accordance with the present invention, there are provided methods of transducing cells comprising providing a flexible closed culture container having cells therein and contacting said cells with a viral-vector in the presence of a multi-functional chemical moiety. Also provided are methods of delivering a functional protein to a subject in need thereof, comprising transducing mammalian cells according to the invention method and introducing said cells into a subject in need thereof. Also provided are cell-culture systems for transducing cells, comprising a flexible closed culture container and a multi-functional chemical moiety therein.

20 Claims, 6 Drawing Sheets

OTHER PUBLICATIONS

Ruoslahti et al., "Alignment of Biologically Active Domains in the Fibronectin Molecule," *J. Biol. Chem.,* 14:7277–7281(1981).

Ruoslahti et al., "Fibronectin: Purification, Immunochemical Properties, and Biological Activities," *Methods in Enzymology,* 82:803–831 (1982).

Ruoslahti et al., "New Perspectives in Cell Adhesion: RGD and Integrins," *Science,* 238:491–497 (1987).

Sackman et al., "Retroviral Mediated Gene Transduction Alters Integrin Expression on Vascular Endothelial Cells," *J. of Surgical Research,* 69:45–50(1997).

Sinha et al., "Characterization of the EBV/C3d Receptor on the Human Jurkat T Cell Line: Evidence for a Novel Transcript[1]," *J. Immunology,* 150:5311–5320(1993).

Takara Shuzo Co., Ltd., "Product description of Retronectin™ T 100 B," *BioWhittaker* pamphlet, pp. 1–3.

Takara Shuzo Co., Ltd., "Product description of RetroNectin™ T 100 A/B," *BioWhittaker* pamphlet, pp. 1–7.

Traycoff et al., "The 30/35 kDa chymotryptic fragment of fibronectin enhances retroviral–mediated gene transfer in purified chronic myelogenous leukemia bone marrow progenitors," *Leukemia,* 11:159–167 (1997).

van Zeijl et al., "A human amphotropic retrovirus receptor is a second member of the gibbon ape leukemia virus receptor family," *Proc. Natl. Acad. Sci. USA,* 91:1168–1172(1994).

Ward et al., "Transfer and Expression of the Human Multiple Drug Resistance Gene in Human CD34+ Cells," *Blood,* 84:1408–1414(1994).

Wayner et al., "Activation–dependent Recognition by Hematopoietic Cells of the LDV Sequence in the V Region of Fibronectin," *J. Cell. Biol.,* 116:489–497(1992).

Weil et al., "Genetic Correction of p67phox Deficient Chronic Granulomatous Disease Using Peripheral Blood Progenitor Cells as a Target for Retrovirus Mediated Gene Transfer," *Blood,* 89:1754–1761 (1997).

Williams et al., "Umbilical Cord Blood Stem Cells as Targets for Genetic Modification: New Therapeutic Approaches to Somatic Gene Therapy," *Blood Cells,* 20:504–516(1994).

Ory et al. A stable human–derived packaging cell line for production of high titer retrovirus/vesicuar stomatitis virus G pseudotypes. Proc. Natl. Acad. Sci. USA vol. 93, pp. 11400–11406, 1996.

Shimizu et al. Regulated expression and binding of three VLA (beta1) integrin receptors on T cells. Nature vol. 345 pp. 250–252, 1990.

Mavilio et al. Peripheral blood lymphocytes as target cells of retroviral vector–mediated gene transfer. Blood vol. 83 pp. 1988–1997, 1994.

Sekhar et al. Retroviral Transduction of CD34–enriched hematopoietic progenitor cells under serum–free conditions. Human Gene Therapy vol. 7 pp. 33–38, 1996.

Non-transduced

Transduced

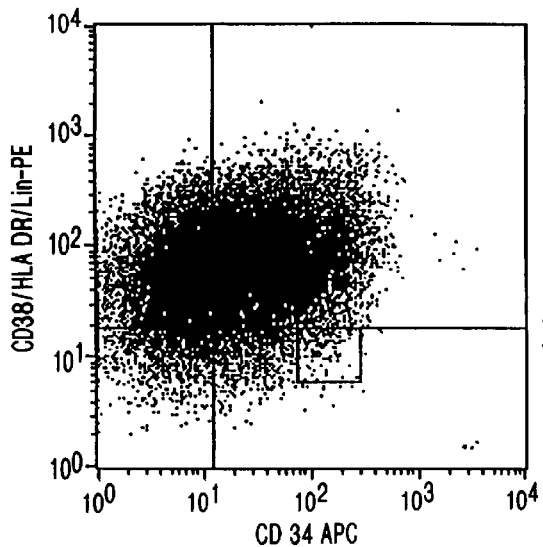
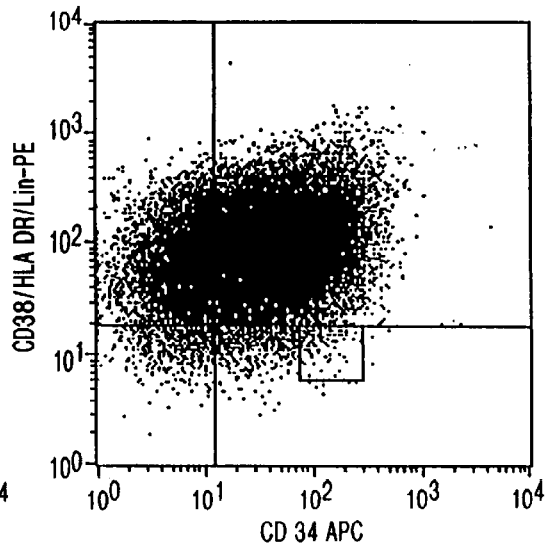
FIG. 4A  FIG. 4B
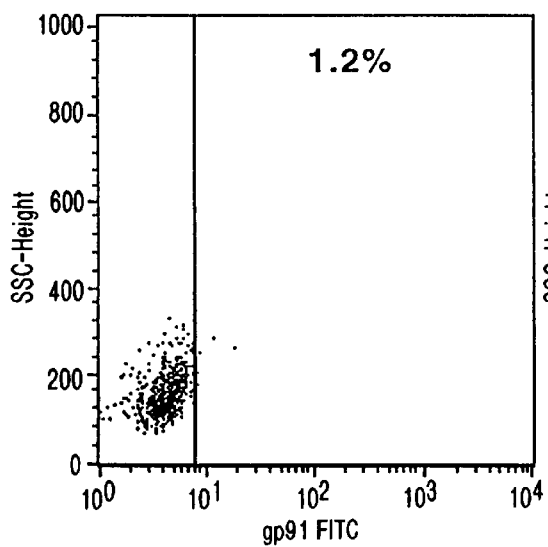
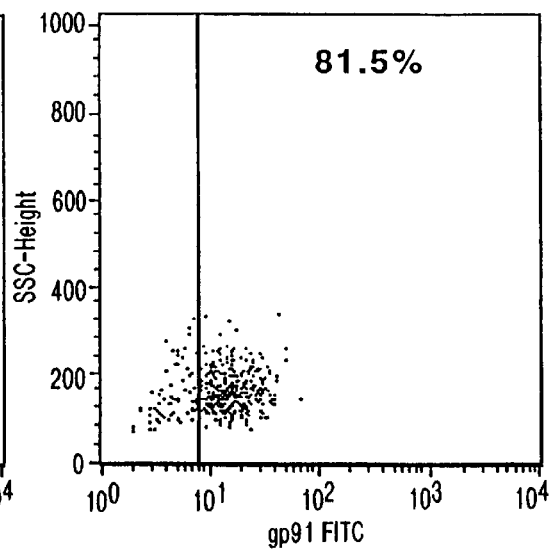
Non-transduced
FIG. 4C
Transduced
FIG. 4D Non-transduced Transduced

SEQUENCE LISTING

<160> NUMBER OF SEQ ID NOS: 4

<210> SEQ ID NO 1
<211> LENGTH: 4
<212> TYPE: PRT
<213> ORGANISM: Homo sapiens

<400> SEQUENCE: 1

Asp Gly Glu Ala
 1

<210> SEQ ID NO 2
<211> LENGTH: 5
<212> TYPE: PRT
<213> ORGANISM: Homo sapiens

<400> SEQUENCE: 2

Tyr Ile Gly Ser Arg
 1               5

<210> SEQ ID NO 3
<211> LENGTH: 4
<212> TYPE: PRT
<213> ORGANISM: Homo sapiens

<400> SEQUENCE: 3

Arg Gly Asp Ser
 1

<210> SEQ ID NO 4
<211> LENGTH: 5
<212> TYPE: PRT
<213> ORGANISM: Homo sapiens

<400> SEQUENCE: 4

Pro His Ser Arg Asn
 1               5

METHOD OF TRANSDUCING MAMMALIAN CELLS, AND PRODUCTS RELATED THERETO

This invention was made with government support under project number Z01 AI 00644 and Z01 AI 00645 funded by the National Institute of Allergy and Infectious Diseases. The government has certain rights in the invention.

BACKGROUND OF THE INVENTION

The present invention relates generally to ex vivo gene therapy and, more specifically, to an improved method for transducing cells with viral-vectors.

The introduction of therapeutic genes into patient cells is a promising approach for the treatment of human diseases such as inherited genetic disorders, cancer, infectious diseases and immune disorders. One approach for introducing therapeutic genes involves isolating a target cell population from an individual, transfering therapeutic genes into the cells while the cells are maintained in culture, testing and selecting for transduced cells, and then reintroducing the genetically engineered cells into a subject. This procedure, known as ex vivo gene therapy, is limited by the current inability to achieve high level gene transfer and expression in clinically relevant numbers of cultured cells.

Transfer of genes into cells can be accomplished by a number of physical and biological methods. Pure DNA will enter cells following electroporation or direct microinjection, or when the DNA is complexed with cationic lipids or calcium phosphate. However, these methods are generally too inefficient and labor intensive for clinical use.

A more efficient method of gene transfer for clinical applications involves transduction of cells by viral-vectors that are genetically engineered to serve as carriers of heterologous genes. The choice of viral-vector depends on the target cell type and transduction approach desired. For example, modified adenovirus and adeno-associated virus can be produced at very high titers and provide for transiently high levels of gene expression in target cells. Replication-defective retroviruses are also used clinically, primarily for transducing cells where stable integration into the host chromosomal DNA is desired. The transferred gene is faithfully replicated and expressed in the progeny of the retrovirally-transduced cells. Other viruses with tropisms for specific cell types and engineered hybrid viruses are also are used in ex vivo gene therapy applications.

Gene therapy is most beneficial when all or the majority of cells that are introduced into a subject contain the desired genetic modification. However, current strategies for transducing cells with viral-vectors have not achieved this goal. One means of improving transduction efficiency is to bring the cultured target cells and the viral-vector into close proximity. For example, co-cultivation of target cells with virus-producing cells has been used to achieve high-efficiency gene transfer. However, co-cultivation raises concerns about the safety of exposing cells that will be introduced into subjects to other cells, as well as concerns about the reproducibility of infection in such a co-culture system.

Ex vivo culture and transduction of cells to date has generally involved the use of culture plates and flasks composed of conventional polystyrene, which is a hard, gas-impermeable plastic. Conventional polystyrene culture vessels are by necessity tied to an open system for regulation of gases dissolved in the culture medium and for regulation of pH of the culture medium. Typically, these conventional culture vessels are maintained in an incubator filled with regulated concentrations of $O_2$ and $CO_2$; the caps or tops of the culture vessels must be offset from the main vessel, and thus open to the environment, in order to admit the ambient gas mixture. As a result, the cell culture is exposed to contamination from the environment.

Thus, there exists a need for improved methods for transducing cells for ex vivo gene therapy applications. The present invention satisfies this need and provides related advantages as well.

BRIEF DESCRIPTION OF THE INVENTION

In accordance with the present invention, there is provided a method of transducing cells comprising providing a flexible closed culture container having cells therein and contacting said cells with a viral-vector in the presence of a multi-functional chemical moiety. The invention method is useful for efficiently transducing clinically relevant numbers of mammalian cells in a closed fluid path system. Also provided are methods of delivering a functional protein to a subject in need thereof, comprising transducing mammalian cells according to the invention method and introducing said cells into a subject in need thereof.

In accordance with another embodiment there is provided a container system for transducing cells, comprising a flexible closed culture container and a multi-functional chemical moiety therein. The invention system is useful in the methods described herein for transducing mammalian cells in a closed fluid path system.

BRIEF DESCRIPTION OF THE FIGURES

FIG. 4 shows the results of a "3-color" flow cytometric analysis in which the percent of primitive cells (CD34 bright, CD38 dim) expressing $gp91^{phox}$ protein for Patient #2 was assessed as described in Example II.

DETAILED DESCRIPTION OF THE INVENTION

Figure 1:
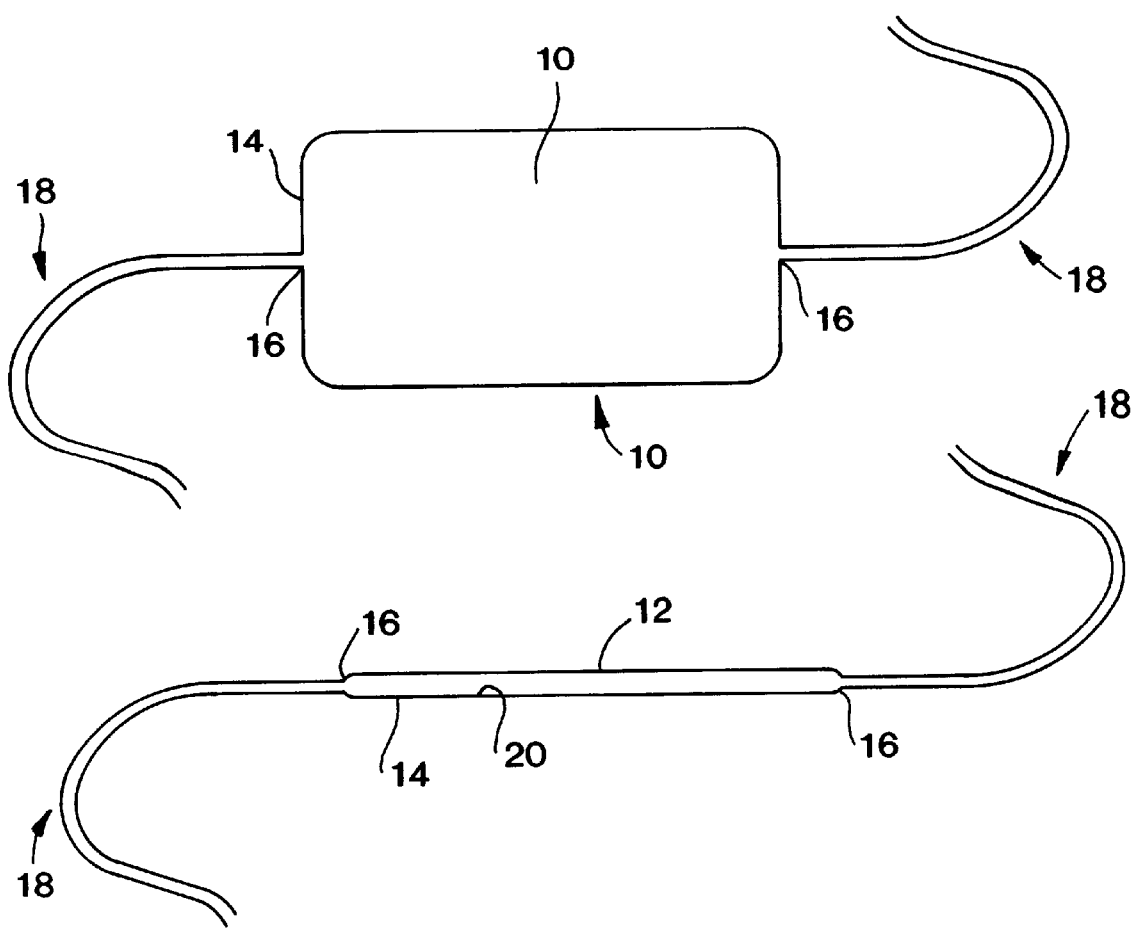
FIG. 1 shows a top view 10 (upper) and side view 12 (lower) of the flexible culture container 14 not drawn to scale, which in this example has two ports 16 with connecting tubing 18 to allow slow continuous flow of liquid medium across the inner surface 20 to allow interaction of cells and/or virus vectors with the surface.
Figure 2:
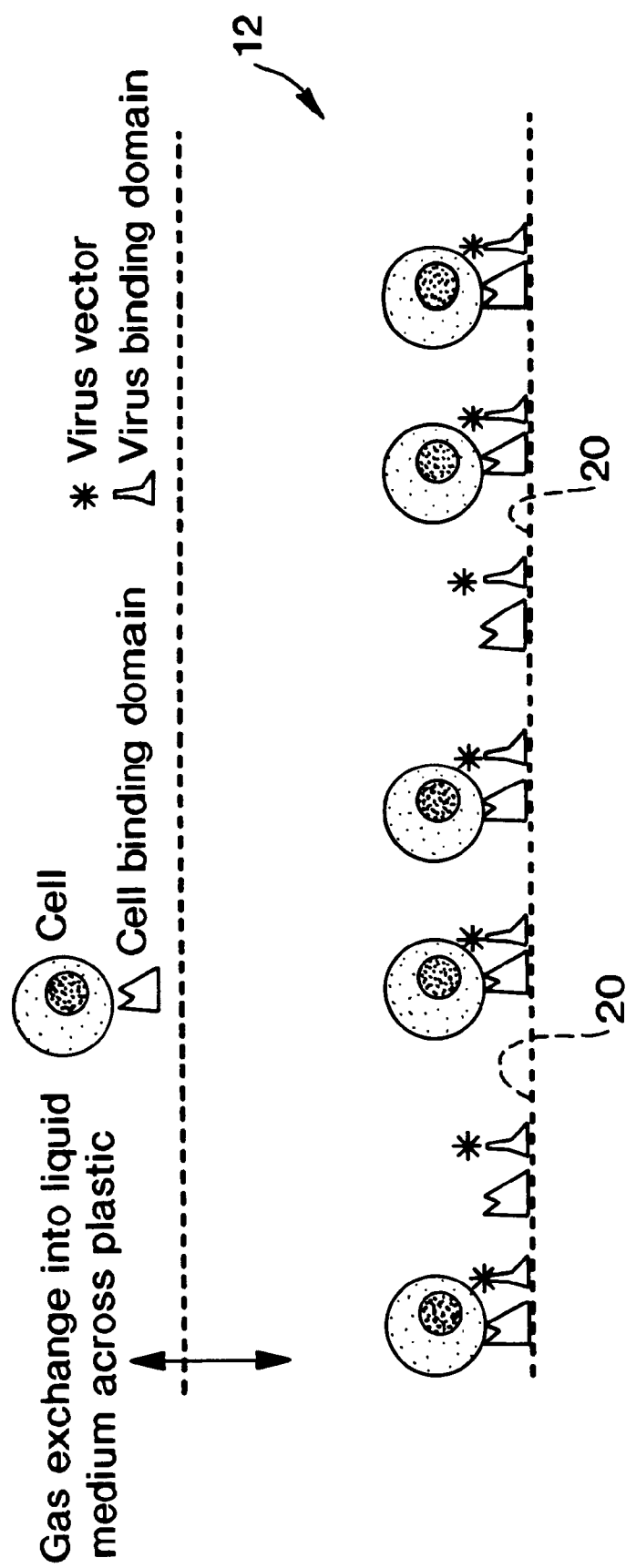
FIG. 2 shows a high magnification schematic of the side view 12 (not drawn to scale) of the flexible culture container 14 of FIG. 1 indicating how target mammalian cells and virus vector both attach to chemical moieties displayed at the inner surface 20 of the gas permeable flexible plastic culture container.
Figure 3A:
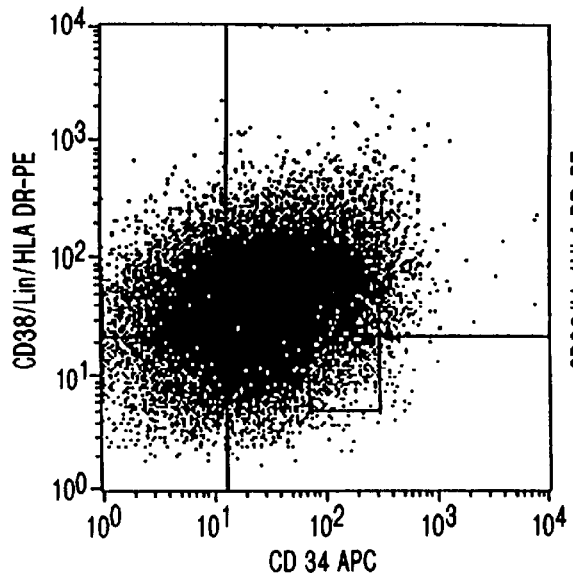
FIG. 3 shows the results of a "3-color" flow cytometric analysis in which the percent of primitive cells (CD34 bright, CD38 dim) expressing $gp91^{phox}$ protein for Patient #1 was assessed as described in Example II.
Figure 3B:
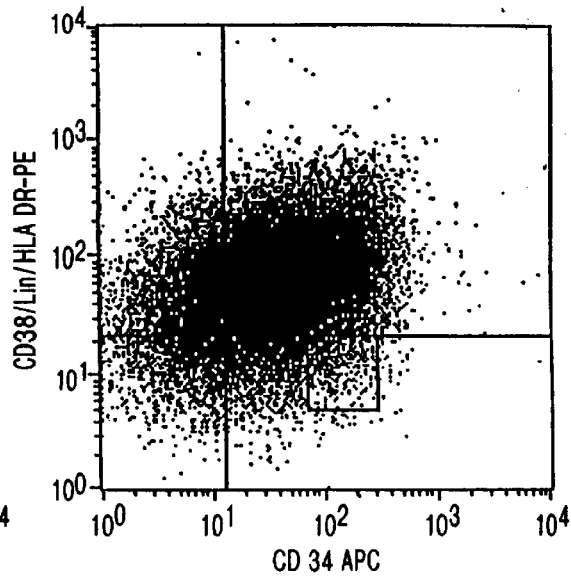
Figure 3C:
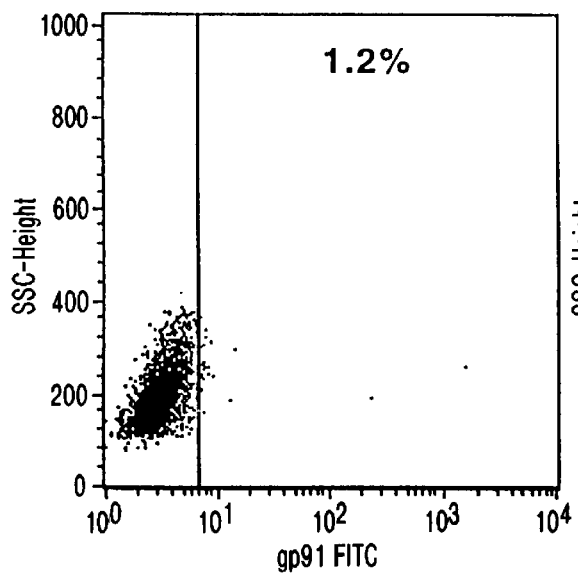
Figure 3D:
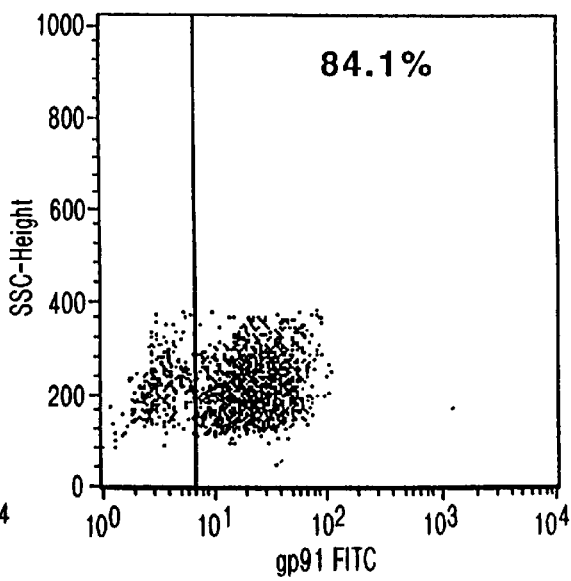
Figure 5A:
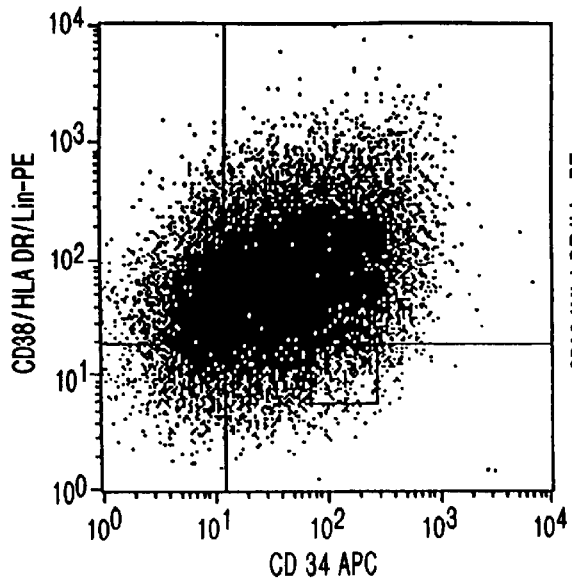
FIG. 5 shows the results of a "3-color" flow cytometric analysis in which the percent of primitive cells (CD34 bright, CD38 dim) expressing $gp91^{phox}$ protein for Patient #3 was assessed as described in Example II.
Figure 5B:
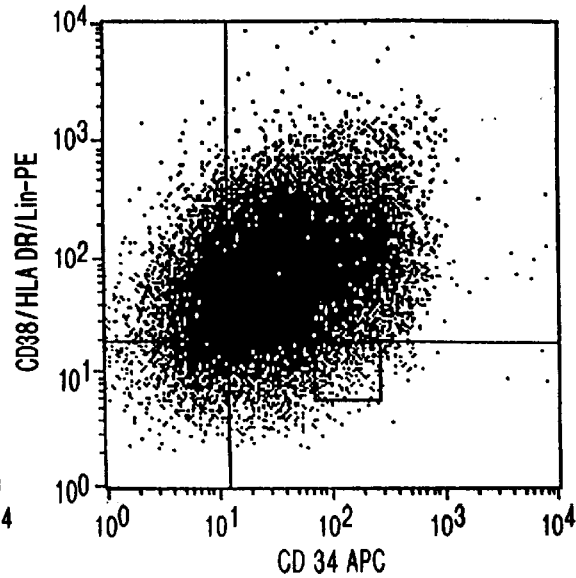
Figure 5C:
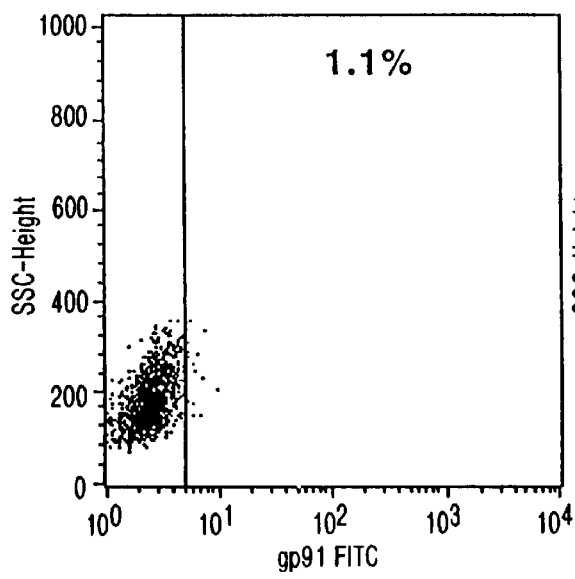
Figure 5D:
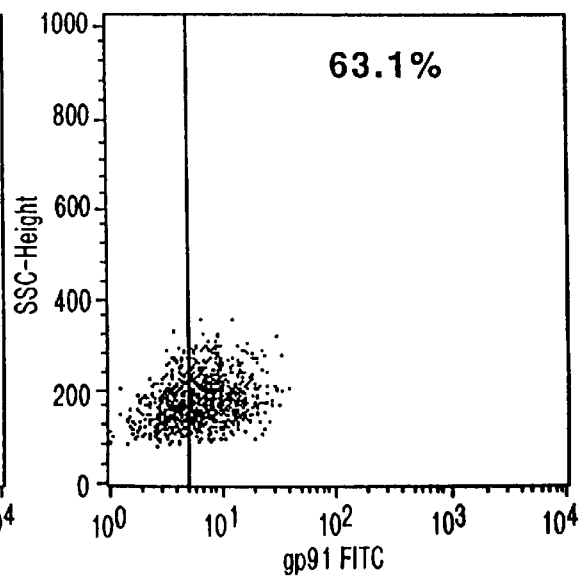

In accordance with the present invention, there is provided a method of transducing mammalian cells, comprising providing a flexible closed culture container having cells therein and contacting the cells with a viral-vector in the presence of a multi-functional chemical moiety. By incorporating a multi-functional chemical moiety into the flexible closed culture container, the invention method advantageously provides a means to increase the viral transduction efficiency of heterologous genes in a clinically safe environment.

As used herein, the phrase "multi-functional chemical moiety" refers to a substantially pure chemical moiety having at least one "cell-surface binding domain" linked to at least one "virus binding domain" and optionally linked to other functional domains such as domains that mediate attachment to a culture container, and the like. The multi-functional chemical moiety functions to colocalize viral-vectors and target cells, which results in the increase in transduction efficiency of the virus relative to the transduction efficiency in the absence of the multi-functional chemical moiety. The multi-functional chemical moiety can be attached, by coating or the like, to the flexible closed culture containers of the invention, or added to the culture medium prior to or during viral transduction.

The flexible closed culture container used in the methods of the present invention provides the advantages of efficiently transducing clinically relevant numbers of mammalian cells in a closed fluid path system. A flexible closed culture container system also advantageously allows for the culture media to be continuously perfused through the container. For example, it may be useful to gradually add fresh media or to dilute undesired products without disturbing the cells cultured therein. By minimizing excessive manipulation of the cells, their viability and engraftment potential can be improved. Similarly, the viral supernatant can be continuously perfused through the container to maximize the contact of virus with the surface of the flexible closed container and with the cells therein. If desired, these solutions can be automatically pumped through the system at a predetermined flow rate.

As used herein, the phrase "flexible closed culture container" refers to a gas-permeable closed container with an inner growing surface of polystyrene. This type of container is exemplified by the PL2417 container (Baxter Immunotherapy, Round Lake, Ill.), described in PCT US95/13943, which is herein incorporated by reference in its entirety.

The inner surface of the flexible container is preferably an ultra-thin layer of polystyrene having a thickness of about 0.0004 inches. The outer surface is composed of a polymer material or a mixture of polymer materials having a thickness of about 0.006 to about 0.008 inches. Such a container preferably has the following physical properties: a flexural modulus of about 10,000–30,000 psi; an oxygen permeability of about 9–15 Barrers; a carbon dioxide permeability of about 40–80 Barrers; a nitrogen permeability of about 10–100 Barrers; a water vapor transmission rate of not more than 20 g mil/100 in$^2$/day; and an optical clarity within the range of about 0.1%–10% as measured by a Hazometer in accordance with ASTM D1003. The containers are also capable of withstanding radiation sterilization.

For adherent cell culture, the growth surface preferably has a surface energy of greater than about 40 dynes/cm. Most adherent cells require a negatively charged growth surface, although some require a positively charged surface. A flexible culture container for adherent cell culture can therefore have either a negatively or positively charged surface.

The exchange of $O_2$ and $CO_2$ in conventional tissue culture dishes is not very efficient, particulary in large culture dishes which could otherwise contain clinically relevant numbers of cells. One advantage of the present invention is that the gas permeability of the flexible closed culture container provides for very efficient exchange of gases. This allows for higher cell viability and more rapid cell proliferation as compared to conventional culture containers.

Conventional, flat tissue culture dishes are inflexible and, therefore, culture in such dishes requires a large volume of medium to ensure that the surface of the dish and the cells thereon are covered. In particular, for the invention transduction procedures, where it is desired to minimize the volume of viral supernatant solution in the culture container, conventional dishes are disadvantageous. The flexibility of the closed culture container advantageously allows for the volume of the media or viral supernatant therein to be minimized. For example, the growing surface of the flexible closed culture container need only be covered with a few millimeters of liquid, following which the air within the container can be sterilely drawn off, in order to ensure that the cells are sufficiently covered.

In one embodiment, the entire cell collection, and preselection if desired, is conducted in a closed fluid path system such as the CS3000/ISOLEX 300i (Baxter Immunotherapy, Irvine, Calif.) which then is aseptically connected to the flexible culture container for the transfer of cells into the container. As used herein, the term "closed fluid path system" refers to an assembly of components, each of which is closed to the ambient environment, and each of which is provided with means for effecting sterile connections among the components. The multi-functional chemical moiety, the cell suspension, the viral-vector and the culture media can be added to or removed from the flexible culture container via sterile connect ports and sterile tubing systems as set forth in FIG. 1. Alternatively, other configurations of ports are also contemplated herein in connection with the invention flexible culture containers. For example, there may be only one port with tubing where medium with cells and/or virus vector enters and exits the same port for static incubation and interaction with the multifunctional chemical domains at the container's inner surface. Tubing may be sealed or sterile connected to pumps and/or reservoir of medium with cells and/or virus vector.

In addition, samples of transduced cells can be aseptically drawn off from the container through sterile-connect ports for analysis. Following cell transduction, concentration into an infusible medium such as PLASMA-LYTE A (Baxter IV Systems, Round Lake, Ill.) can be carried out aseptically via sterile-connect ports, and the washed and concentrated cells can be infused directly via the patient's intravenous line without exposing the cells to the environment, or the personnel to the cells.

As used herein, the term "linked" or "linkage," when referring to a multi-functional chemical moiety, refers to an operative connection between a cell-surface binding domain and a virus-binding domain such that a target cell and a viral-vector are co-localized for efficient transduction. Depending on the particular cell-surface binding domain and virus-binding domain, the linkage can be accomplished by chemical cross-linking using agents with two or more reactive groups at opposite ends of a linker arm. These cross-linking agents react with functional groups in the cell surface and virus binding domain fragments to form stable covalent bonds. Appropriate cross-linking reagents are known in the art and are readily available commercially.

A multi-functional chemical moiety that comprises two or more peptide subunits can also be recombinantly produced by the expression of a nucleic acid sequence encoding a cell binding domain and a virus binding domain on a single polypeptide chain. A multi-functional chemical moiety can also be directly synthesized by methods known in the art.

In one embodiment, a cell-surface binding domain and a virus-binding domain are "linked" by their independent attachment to the surface of a flexible culture container, such that the surface of the container functions as the multi-functional chemical moiety. The cell-surface binding domain and the virus-binding domain can be attached, either sequentially or together, to the container so long as each domain is attached to the surface of the container. Each of the cell-surface binding and virus-binding domains are attached to the surface of the container in sufficient quantity to allow each domain to be in close enough proximity to each other to function to co-localize the viral-vectors and cells.

As used herein, the phrase "cell-surface binding domain" refers to a moiety that has the ability to attach to the surface of a cell such that domains other than the cell-surface domain are in close proximity to the cell surface and available to interact with one or more other surfaces. The attachment to the cell surface can be, for example, an attachment to cell membrane lipids or to proteins or glycoproteins present at the cell surface. For example, the attachment can be via binding to receptors on the cell surface, such as integrins, growth factor and cytokine receptors, and the like.

Exemplary cell-surface binding domains are present in cell-surface binding molecules such as growth factors and cytokines (eg., EGF, FGFs, PDGF, insulin, IGFs, TGFs, VEGF, NGF, G-CSF, GM-CSF, interferons, interleukins, TNFs, and the like, and cell-surface binding fragments and analogs thereof); extracellular matrix proteins (eg., fibronectin, collagen, laminin, vitronectin, thrombospondin, von Willebrand factor, fibrinogen, tenascin, osteopontin and the like, and cell-surface binding fragments and analogs thereof); antibodies and antibody fragments that bind cell surface molecules; lectins; and cell-cell adhesion molecules (eg., cadherins, fasciclins and ICAMs, and the like, and cell binding fragments and analogs thereof).

Particular cell-surface binding domains of cell-surface binding molecules have been characterized and can be used in a method of the invention. For example, many extracellular matrix adhesion proteins contain an Arg-Gly-Asp sequence that mediates their interaction with cell surface integrins (Ruoslahti et al., Science 238:491–497 (1987)). Peptides including this sequence are cell-surface binding fragments. Other cell binding domains in extracellular matrix proteins are also recognized, such as the TSPN18 and TSPN28 recombinant fragments from the amino terminus of thrombospondin (Incardona et al., J. Cell. Biochem., 62:431–442 (1996)); the collagen peptide motif DGEA (SEQ ID NO:1) (Matrix Biol., 16:273–283 (1997)); the pentapeptide YIGSR (SEQ ID NO:2) of laminin (Graf et al., Cell, 48:989–996 (1987)), and the like.

A preferred cell-surface binding domain of the invention is a cell-surface binding fragment of fibronectin. Several fragments of fibronectin bind to integrins on the surface of cells. An exemplary cell-surface binding fragment of fibronectin is a fragment containing the sequence Arg-Gly-Asp-Ser (RGDS) (SEQ ID NO:3) and optionally containing the sequence Pro-His-Ser-Arg-Asn (PHSRN) (SEQ ID NO:4). Such a fragment may also include all or part of the ninth and tenth fibronectin Type III repeats. A cell-surface binding fragment of fibronectin can also be a VLA-4 ($\alpha 4\beta 1$) integrin binding site CS-1 (connecting segment-1) within the alternatively spliced IIICS region, or a cell binding fragment therefrom containing the tripeptide leu-asp-val (LDV) (Wayner et al., J. Cell Biol., 116:489–497 (1992)). A further cell binding fragment of fibronectin is the N-terminal matrix assembly site that binds VLA-5 ($\alpha 5\beta 1$) integrin (Hocking et al., J. Cell Biol., 141:241–253 (1998)). A cell-surface binding fragment of the invention can include one or more of these cell binding domains of fibronectin.

A multi-functional chemical moiety also includes a virus-binding domain. As used herein, the term "virus-binding domain" refers to a moiety that attaches to the surface of a virus such that domains other than the virus-binding domain are in close proximity to the virus surface and available to interact with one or more other surfaces. Exemplary virus-binding domains are found in virus-binding molecules such as virus receptor molecules (eg., CD4, a receptor for HIV; CR2, a receptor for EBV (Sinha et al., J. Immunol., 150:5311–5320 (1993)); GLVR-2 or Pit2, a receptor for amphotrophic murine leukemia viruses (van Zeijl et al., Proc. Natl. Acad. Sci. USA, 91:1168–1172 (1994), Chien et al., J. Virology, 71:4564–4570 (1997)); CAR, a receptor for coxsackievirus and adenovirus (Bergelson et al., Science, 275:1320–1323 (1997)); and the like) and virus-binding fragments thereof; antibodies and antibody fragments that bind virus surface molecules such as env gene products; heparan sulfate; and heparin binding domains of extracellular matrix molecules. Another exemplary virus-binding domain is the high affinity heparin-binding domain II of human fibronection (FN type III repeats 12, 13, 14), and virus-binding fragments thereof.

Cell -surface or virus- binding domains can be modified so long as cell or virus binding activity, respectively, is maintained. Such modifications can include, for example, additions, deletions or substitutions of natural or non-naturally occuring amino acids. Structural analogs of natural cell-surface or virus binding domains, such as peptide mimetics, can also be produced and are included within the invention, so long as cell or virus binding activity is maintained.

A cell surface or virus binding domain can be produced by proteolysis or chemical cleavage of a molecule containing such a domain and isolation of the molecule. A cell surface or virus binding domain can also be recombinantly produced using an appropriate vector containing a nucleic acid sequence encoding such a domain. A cell surface or virus binding domain can also be directly synthesized by synthesis methods known in the art.

A preferred multi-functional moiety suitable for cell transduction is an extracellular matrix molecule, or fragment therefrom, that contains both a cell surface binding domain and a virus binding domain. An exemplary multi-functional moiety is human fibronectin, whose amino acid sequence is set forth in Kornblihtt et al., The EMBO J., 4(7):1755–1759 (1985) Fibronectin can be purified from plasma, recombinantly produced, or obtained commercially. "Multi-functional fragments" of fibronectin, which contain one or more virus-binding and one or more cell-surface binding domains of fibronectin, are also included within the invention. These fragments can be produced recombinantly or by proteolysis of fibronectin.

Multi-functional fragments of fibronectin include fragments such as the 30/35 kDa carboxy-terminal chymotryptic fragment of fibronectin (Ruoslahti et al., J. Biol. Chem. 256:7277–7281 (1981); Ruoslahti et al., Methods Enzymol. 82:803–831 (1982)). Multi-functional fragments of fibronectin also include recombinantly produced fragments such as CH-296, H-296 and CH-271 fragments (Hanenburg et al., *Nature Medicine* 2:876–882). The fibronectin fragment CH-296 consists of amino acids 1239 to 1515 recombinantly fused to amino acids 1690 to 1985 of human fibronectin. The fibronectin fragment H-296 consists of amino acids 1690 to 1985 of human fibronectin. The fibronectin fragment CH-271 consists of amino acid 1239 to 1515 recombinantly fused to amino acids 1690 to 1960 of human fibronectin. The sequences of fibronectin fragments CH-296, H-296 and CH-271 are set forth in U.S. Pat. No. 5,198,423, which is incorporated herein by reference in its entirety.

As used herein, the term "cells" refers to mammalian cells capable of being maintained in culture and of being transduced with viral-vectors. The term is intended to include both primary cells and established cell lines. Preferred cells of the invention are human cells and may be of any relevant tissue origin. Appropriate target cells for gene transduction include progenitor cells from various tissues that have the capacity for self-renewal, including keratinocytes, fibroblasts, hepatocytes and myoblasts. Particularly preferred cells are human hematopoietic cells, such as hematopoietic stem cells, lymphocytes, dendritic cells and monocytes.

The phrase "hematopoietic cells" refers to cells that are, or differentiate to become, blood and immune cells. Such cells include, for example, stem cells such as pluripotent hematopoietic stem cells, including CD34+ stem cells, lymphoid stem cells and myeloid stem cells. The phrase "hematopoietic cells" as used herein also includes progenitor and immature cells such as T and B cell progenitors, granulocyte-monocyte progenitors, eosinophil progenitors, basophil progenitors, megakaryocytes and erythroid progenitors. Hematopoietic cells of the invention also include mature cells such as B and T lymphocytes, dendritic cells, monocytes, macrophages, neutrophils, eosinophils and mast cells. Particularly preferred hematopoietic cells are lymphocytes, dendritic cells and monocytes.

Hematopoietic cells can be obtained from various tissue and fluid sources, including, for example, embryonic yolk sac, fetal liver, spleen, thymus, lymph, bone marrow, umbilical cord blood and peripheral blood. A preferred source of hematopoietic cells is peripheral blood obtained by apheresis. Dendritic cells can also be obtained from non-lymphoid organs such as the skin.

Transduction of cells by a method of the invention can be performed in unselected cell populations. Alternatively, particular cell types can be selectively enriched prior to transduction to reduce the amount of virus required and to increase the transduction rate relative to unselected populations. Cells that express a specific protein on their surfaces can readily be isolated by interaction with a specific binding agent such as, for example, a specific antibody. As an example, CD34+ hematopoietic stem cells can be selectively enriched prior to transduction by virtue of the presence of CD34+ antigen on the surface of these cells, which can be targeted with a CD34+ monoclonal antibody. Various means for CD34+ cell selection are described in the following patent documents: U.S. Pat. No. 5,536,475; U.S. Pat No. 5,240,856; U.S. Pat. No. 5,411,863, and the like.

Cells that can be transduced by a method of the invention further include cells that can be differentiated in culture along a particular cell lineage, such as dendritic cells. For example, mononuclear cells can be isolated from a leukapheresis product by density gradient centrifugation, and cultured in the presence of hematopoietic growth factors such as IL-4, GM-CSF, or TNF-α in order to promote the proliferation and differentiation of dendritic cells.

Transduction by a method of the invention can be performed in the presence of additives such as dextran sulfate or "polycations" that enhance the efficiency of cell transduction in the presence of a multi-functional chemical moiety. As used herein, the term "polycations" includes positively charged compositions such as polycationic lipids, protamine sulfate, poly-L-lysine, poly-L-arginine, polybrene, chitosan, poly(ethyleneimine), polymers incorporating basic groups such as amines, and the like. Appropriate polycations and concentrations thereof can be determined by one skilled in the art to maximize transduction efficiency and minimize cell toxicity. A preferred polycation is protamine, which can be used at a concentration of between 0.5 μg/ml and 10 μg/ml, more preferably at about 6 μg/ml.

Cell transduction by a method of the invention can be performed in serum-free, animal protein free medium. The serum-free, animal protein-free base medium can be a proprietary medium such as X-VIVO 10 or X-VIVO 15 (BioWhittaker, Walkersville, Md.), Hematopoietic Stem Cell-SFM media (GibcoBRL, Grand Island, N.Y.) or can be of any formulation which is favorable to mammalian cell culture. Serum-free media are described in the following patent documents: WO 95/00632; U.S. Pat No. 5,405,772; PCT US94/09622. The serum-free base medium can contain clinical grade human serum albumin in a concentration of about 0.5–5.0%, usually about 1.0% (w/v). Clinical grade albumin derived from human serum, such as BUMINATE (Baxter Hyland, Glendale, Calif.), is so highly purified and isolated from other serum components that it is herein considered serum-free.

Media formulations that are serum-free and animal protein-free are free from animal proteins such as those present in fetal calf serum (FCS) and bovine serum albumin (BSA), which are traditional additives in cell culture. The absence of animal proteins will abrogate contact of the cells with a foreign protein which could detrimentally affect their immune function or otherwise change their nature. Animal protein-free media formulations will also abrogate the risk of returning highly immunogenic animal proteins to the subject, which could cause anaphylactic shock and death.

As used herein the term "transducing" refers to introduction of a particular nucleic acid sequence contained in a "viral-vector" into cells. Transduction by a method of the invention involves contacting cells with a viral-vector in the presence of a multi-functional chemical moiety such that the viral nucleic acid enters the cell and can be expressed therein. Viral based systems provide the advantage of being able to introduce relatively high levels of a heterologous nucleic acid into a variety of cells.

Suitable viral-vectors for transducing mammalian cells are well known in the art. These viral-vectors include, for example, Herpes simplex virus vectors (eg., U.S. Pat. Nos. 5,672,344 and 5,501,979), Vaccinia virus vectors (eg., Piccini et al., *Meth. in Enzymology*, 153:545–563 (1987)); Hepatitis B-based vectors (eg. Chaisomchit et al., *Gene Therapy*, 4:1330–1340 (1997)); Cytomegalovirus vectors (eg., Mocarski et al., in *Viral-vectors*, Y. Gluzman and S. H. Hughes, Eds., Cold Spring Harbor Laboratory, Cold Spring Harbor, N.Y., 1988, pp. 78–84); Adenovirus vectors (eg., U.S. Pat. Nos. 5,731,172 and 5,707,618); Adeno-associated virus vectors (eg., U.S. Pat. Nos. 5,741,683; 5,478,745; and 5,756,283); Lentiviral vectors (eg., Naldini et al., *Proc. Natl.*

Acad. Sci. USA, 93:11382–11388 (1996)); Parvovirus vectors (eg., U.S. Pat. No. 5,585,254); Retrovirus vectors (eg., U.S. Pat. Nos. 4,405,712; 4,650,764; 5,686,279; 5,591,624; 5,693,508; 5,747,323; 5,667,998;, 5,672,510; 5,580,766 and 5,716,826), and the like.

Particularly preferred viral-vectors for a method of the invention are replication-defective retroviral-vectors. Genes transferred in retroviral vectors are integrated into chromosomal DNA and are therefore faithfully replicated and expressed in progeny cells. These vectors are capable of mediating stable gene integration in a wide range of target cell types without unacceptable gene deletion or gene rearrangement in the host genome. Replication-defective retroviral vectors generally do not contain gag, pol or env gene sequences, and are incapable of producing progeny virus after transduction of the target cell. Replication-defective retroviral vectors can be derived from amphotrophic viruses, such as the Moloney Murine Leukemia Virus (Mo-MuLV). An especially preferred viral-vector is the MFGS retrovirus vector (available from Cell Genesys, Foster City, Calif.; Weil et al., *Blood*, 89:1754–1761 (1997)).

Retroviral vectors are packaged in special "packaging" cell lines that are genetically modified to produce the gag, pol and env proteins required to make a complete virus particle. The gene of interest is inserted into the retrovirus vector DNA, which is transfected into a packaging line to obtain clones of cells that package and shed recombinant replication-defective retrovirus. Packaging cell lines for replication-defective retroviruses can contain CRIP packaging plasmids, such as the ψ-CRIP NIH 3T3 murine fibroblast line (Danos et al., *Proc. Natl. Acad. Sci. USA*, 85:6460–6464 (1988)). A preferred packaging cell line is the amphotropic 293-SPA human embryonic kidney cell packaging line (Davis et al., *Hum. Gene Therapy*, 8:1459–1467 (1997)).

Viral-vectors of the invention can also be packaged for the production of pseudoviruses. Such hybrid viruses contain the nucleic acid and certain protein-components of one type of virus enclosed in the capsid or outer coat of a different type of virus. Pseudotype viruses are advantageous in combining useful features of two or more viruses. For example, a viral nucleic acid that is particularly amenable for cloning or for replication within a target cell can be packaged within a viral coat that provides for enhanced robustness or a particular cell tropism. A particular example of a pseudotype virus is a retroviral vector packaged with the vesicular stomatitis virus-G (VSV-G) envelope.

In accordance with another embodiment of the present invention, there is provided a container system for transducing cells, comprising a flexible closed culture container and a multi-functional chemical moiety therein. A flexible closed culture container having a multi-functional chemical moiety therein can be prepared, for example, in an aqueous buffer such as phosphate-buffered saline (PBS). The solution containing the multi-functional chemical moiety can be applied to the flexible culture container in sufficient volume to cover the growing surface of the container, and incubated at room temperature or at 37° C. for several hours. For coating a flexible culture container, an appropriate concentration of multi-functional chemical moiety is between about 1 μg/ml and 1 mg/ml, preferably between about 10 μg/ml and 200 μg/ml. The solution can optionally be removed following incubation. Alternatively, the multi-functional chemical moiety can be added to the cell culture medium or the viral supernatant preceding or during the transduction procedure.

In accordance with yet another embodiment of the present invention, there is provided a method of delivering a functional protein to a subject in need thereof, comprising transducing cells within a flexible closed culture container having cells therein, according to a method of the present invention, and introducing the transduced cells into a subject in need thereof.

Typically, a subject in need thereof is a patient having a "pathology," which is an abnormal disease state characterized by, for example, genetic defects, infection, neoplasia, altered immune function, tissue damage, and the like. Thus, in accordance with the invention methods of delivering functional proteins to subjects in need thereof, a pathology can be treated by introducing cells transduced with appropriate genes into a patient. For example, a genetic deficiency can be treated by introducing into a subject cells transduced with nucleic acid sequences that encode a wild-type copy of a defective gene. These nucleic acid sequences express proteins, such as structural proteins or enzymes, that compensate for the genetic deficiency. Therapeutic genes need not be delivered to the cell type that is itself affected. For example, cells that are engineered to express and secrete various enzymes can be reimplanted in various areas of the body to produce secreted products.

Representative genetic deficiencies that can be treated by a method of the invention include, for example, severe combined immunodeficiency caused by adenosine deaminase (ADA) deficiency or purine nucleoside phosphorylase (PNP) deficiency, chronic granulomatous disease (CGD) caused by phox subunit gene deficiency, diabetes caused by insulin deficiency, hypercholesterolemia caused by LDL receptor deficiency, hemophilia caused by Factor IX deficiency, and thalassemias and anemias caused by globin gene deficiencies.

Neoplasias can also be treated by a method of the invention. Genetically modified cells can be introduced that express a gene that contributes to the inhibition of neoplastic cell growth. Such genes can be tumor suppressors such as p53 and Rb; encode anti-sense or ribozyme molecules that inhibit oncogene expression; induce drug sensitivity to tumors; increase the immune response to tumors; or encode cytotoxic products. For example, cells can be transduced with Fas ligand for the killing of Fas-expressing tumors. Tumor cells can also be transduced with genes that make them sensitive to killing by the subsequent administration of a chemotherapeutic drug. For example, the herpes virus thymidine kinase (HSVTK) can be introduced into tumor cells and the patients treated systemically with gancyclovir. A "bystander effect" provides killing of both transduced and non-transduced tumor cells. Tumor cells can also be transduced with cytokine genes, such as IL-2 and GM-CSF, and injected into subjects as vaccines to enhance anti-tumor immune responses.

Proteins or peptide fragments thereof that are characteristic of particular cell types can be recognized by the immune system when appropriately presented by antigen-presenting cells. For example, a cell can be transduced with a tumor-specific molecule and returned to the individual to initiate humoral and cell-mediated immune responses for the elimination of neoplastic cells bearing that molecule. Similarly, proteins or peptides that are characteristic of cells infected by viruses and other pathogens can be appropriately presented to the immune system following transduction with a viral-vector encoding the characteristic protein or peptide.

The toxicity of many chemotherapeutic agents is due to myeloablation with concomitant leukopenia and/or thrombocytopenia, and creating a population of hematopoietic stem cells that are resistant to specific drugs is advantageous. Therefore, normal cells, particularly normal hematopoietic stem cells, can be transduced with genes that confer resistance to chemotherapeutic agents as an adjunct to traditional cancer therapy. For example, patient cells can be transduced with genes encoding multiple drug resistance (such as MDR and MRP), dihydrofolate reductase, methylguanine methyltransferase, aldehyde dehydrogenase and the like, and increased doses of chemotherapeutic agents can be given.

Disorders of the immune system that can be treated by a method of the invention include autoimmune disorders. Numerous disorders are believed to result from autoimmune mechanisms, including, for example, rheumatoid arthritis, multiple sclerosis, type I diabetes, systemic lupus erythematosus, myasthenia gravis, psoriasis and pemphigus vulgaris. Immune cells can be transduced with autoantigens which are appropriately presented to the host immune system to induce tolerance to the autoantigen, thereby treating the autoimmune disease.

Disorders of the immune system that can be treated by a method of the invention also include disorders caused by rejection of allogeneic cells or tissues. Allogeneic MHC molecules are highly immunogenic and will trigger rejection of the grafted cells if there are too many mismatches. Therefore, rejection of allogeneic cells can be prevented by transducing the allogeneic cells with MHC molecules that match the recipient or with molecules that block the mismatched MHC molecules.

Infectious disorders can be treated by introducing cells into a subject that have been transduced with genes that inhibit viral infection, replication or assembly. Such genes encode, for example, anti-viral antibodies, mutant viral receptors that prevent viral attachment, anti-viral ribozymes, anti-sense transcripts, and the like. For example, AIDS and HIV-1 pathologies can be treated or prevented by transducing hematopoietic stem cells with dominant-negative mutant of HIV gag, rev or int linked to an HIV promoter. The differentiated cells derived from this transduced population are protected from HIV infection. Similar strategies could also be employed to treat or prevent other infectious diseases.

Cardiovascular diseases are also amenable to gene therapy. For example, the introduction of cells transduced with a gene encoding lecithin:cholesterol acyltransferase can reduce atherosclerosis; and the genes encoding nitric oxide synthase, Fas ligand and GAX (growth arrest-specific homeobox) delivered to endothelial tissues can prevent or treat restenosis.

Pathologies that can be treated by a method of the invention particularly include disorders of the hematopoietic system. Hematopoietic cells are straightforward to isolate and contain populations of stem cells that can divide and differentiate to repopulate the hematopoietic system. As used herein the term "hematopoietic disorder" includes disorders affecting hematopoietic cells, including: neoplasias such as Hodgkin's and non-Hodgkin's B and T cell lymphomas and leukemias; genetic disorders such as thalassemias, Fanconi anemia, adenosine deaminase (ADA) deficiency, X-linked severe combined immunodeficiency syndrome (X-SCID), chronic granulomatous disease (CGD), Gaucher's disease, Hurler's syndrome, sickle cell disease and the like; infectious disorders such as AIDS; as well as hematopoietic and immune dysfunctions caused by chemotherapy and radiation treatment.

Chronic granulomatous disease (CGD) is an inherited deficiency of the immune system caused by the failure of blood neutrophil leukocytes to produce microbicidal hydrogen peroxide. CGD patient blood neutrophils have a defect in the NADPH oxidase enzyme required for production of superoxide, the chemical precursor of hydrogen peroxide. The phagocyte NADPH oxidase is composed of several protein subunits. A genetic mutation affecting production of any one of the subunits results in the patient having CGD. The two most common forms of CGD are the X-linked variety resulting from defects in the gene encoding the gp91$^{phox}$ oxidase subunit protein and an autosomal recessive variety resulting from defects in the gene encoding the p47$^{phox}$ oxidase subunit protein. Since hematopoietic CD34+ stem cells give rise to the circulating blood neutrophils, the invention methods have been employed to permit CGD patient CD34+ stem cells to produce the missing oxidase subunit could correct the oxidase defect of CGD because functionally corrected neutrophils are produced from the gene corrected stem cells by proliferation and differentiation.

Cells that have been transduced by a method of the invention are introduced into a subject in need thereof to effectively treat the pathology. The transduced cells can be cells previously obtained from the same individual or an MHC-matched individual. Introduction of cells into a subject is generally accomplished by intravenous infusion of cells in an infusion solution. A preferred infusion solution is PLASMALYTE infusion solution (available from Baxter HealthCare) containing 1% human serum albumin.

The invention will now be described in greater detail by reference to the following non-limiting examples. All U.S. patents and all publications mentioned herein are incorporated in their entirety by reference thereto.

EXAMPLE I

Transduction of CD34+ Cells in Flexible Containers in the Presence of a Multi-Functional Chemical Moiety This example demonstrates that human cells can be efficiently transduced in flexible closed culture containers in the presence of a multi-functional chemical moiety.

The efficiencies of transducing human hematopoietic stem cells in fibronectin fragment-coated and uncoated flexible closed culture containers and conventional culture plates were compared. Specifically, the following four culture container conditions were compared: 1) a fibronectin fragment-coated gas-permeable flexible plastic container; 2) an uncoated gas-permeable flexible plastic container; 3) a fibronectin fragment-coated conventional hard plastic tissue culture plate; and 4) an uncoated conventional hard plastic tissue culture plate. The multifunctional chemical moiety used to coat the surface of the culture vessel was a recombinant human carboxyl-terminal fragment of fibronectin designated CH-296 (available from BioWhittaker Co.; see U.S. Pat. No. 5,198,423). The Baxter PL2417 gas-permeable flexible plastic culture containers used were the 120 ml sized (15 cm×7.5 cm surface area per side holding 120 ml fully inflated).

The multi-functional chemical moiety CH-296 was dissolved in phosphate buffered saline with added HEPES buffer (PBS at pH 7.2–7.4) at a concentration of 100 µg/ml and 10 ml of this solution introduced into the PL2417 container using a 22 gauge needle and 20 cc syringe. Overnight incubation at room temperature allowed the CH-296 fibronectin fragment to coat the inner surface of the PL2417 container by electrostatic attraction. At that time the CH-296 fibronectin fragment solution was removed and the containers were blocked for 30 min with 15 ml of 2% bovine serum albumin. The containers were then washed three times with 40 ml of Hank's buffered saline solution (HBSS) containing HEPES buffer. The 6-well conventional hard plastic tissue culture plates (35 mm diameter wells) were similarly treated with 5 ml of the solution of PBS with fibronectin fragment CH-296 to allow coating of the surface, followed by blocking and washing. As controls, uncoated PL2417 flexible gas-permeable containers or 6-well conventional tissue culture plates were similarly blocked and washed.

While the above-described conditions were used in the initial experiments, subsequent studies have demonstrated similar results can be obtained: 1.) when coating with PBS solutions without HEPES, but containing 20 to 100 μg/ml CH-296; 2.) when the coating times are 2 hours to overnight; and 3.) when the blocking solution is 1% human serum albumin (HSA) in PBS instead of 2% bovine serum albumin in HBSS with HEPES.

Initial transduction efficiency experiments were performed with human CD34+ hematopoietic stem cell cells obtained from the peripheral blood of normal donors that had been treated with 5 or 6 daily doses of granulocyte colony stimulating factor (G-CSF, Amgen) to mobilize stem cells from the peripheral blood. In subsequent experiments, the peripheral blood CD34+ stem cells were similarly obtained from patients with the inherited immune deficiency known as X-linked gp91$^{phox}$-deficient chronic granulomatous disease. Volunteers or patients were subjected to an apheresis procedure on day 5 or 6 of G-CSF mobilization to harvest a mononuclear cell fraction enriched for the stem cells using the CS3000 Plus blood cell separator device (Baxter Healthcare, Fenwal Division, Deerfield, Ill.). This apheresis product was subjected to an antibody selection procedure using monoclonal antibody directed at the CD34+ antigen following manufacturer's instructions using the ISOLEX 300 SA immunomagnetic stem cell selection system device (Baxter Healthcare, Fenwal Division, Deerfield, Ill.). The purified CD34+ cells were cryopreserved in 10% DMSO/90% fetal bovine serum in the vapor phase over liquid nitrogen until use.

For the initial studies of transduction efficiency of CD34+ cells in the fibronectin fragment coated PL2417 flexible gas-permeable containers, the MFGS-gp91$_{phox}$ amphotropic retrovirus vector was used. The MFGS retrovirus vector backbone has been described previously and has been used in a variety of clinical gene therapy settings (see, e.g., Malech et al. *PNAS, USA* 94:12133–12138, 1997) The retrovirus vector was produced using the 293 SPA packaging cell line, which is a human embryonic kidney cell line engineered to produce the virus packaging proteins: gag, pol and amphotropic envelope (see Davis et al., *Human Gene Therapy* 8:1459–1467, 1997). The MFGS-gp91$^{phox}$ retrovirus vector was collected from confluent producer cell layers of the 293–SPA amphotropic packaging line over a 12 hour period in X-VIVO 10 medium (a serum-free, animal protein free medium available from BioWhittaker) supplemented with 1% human serum albumin (HSA) and is designated as Vector Supernatant (VSN). This VSN is the vector used in all of the examples/experiments described below.

In particular, the MFGS-gp91$^{phox}$ vector contains the coding sequence of human gp91$^{phox}$, one of the subunits of the phagocytic blood cell NADPH oxidase enzyme (see Li, F, et al. Blood 84:53, 1994). This vector was specifically designed for clinical application for gene therapy to treat the gp91$^{phox}$ protein deficient form of the inherited immune deficiency known as X-linked chronic granulomatous disease. It is also a convenient marker gene because an FITC conjugated anti-gp91$^{phox}$ monoclonal antibody (antibody 7D5) can be used in a flow cytometric assay to detect expression of this therapeutic protein as a marker at the surface of cells successfully transduced with this retrovirus vector.

It is known that patients with X-linked CGD have a genetic defect resulting in failure of mature differentiated phagocytic cells (e.g. neutrophils) to produce gp91$^{phox}$ and therefore fail to generate the microbicidal oxidants, superoxide and hydrogen peroxide. MFGS-gp91$^{phox}$ amphotropic retrovirus transduction of CD34+ cells from patients with gp91$^{phox}$-deficient X-linked CGD with MFGS-gp91$^{phox}$ retrovirus vector can be assessed either by using flow cytometry to detect gp91$^{phox}$ expression in the cultured CD34+ cells or by using a flow cytometry assay of oxidase activation (oxidant production) in neutrophils differentiated from transduced CD34+ cells. However, even in transduced normal CD34+ cells the early expression of gp91$^{phox}$ detected by antibody labelling and flow cytometry can be used as a marker to indicate successful transduction by this retrovirus vector. This is because this protein is produced only later in differentiation of myeloid cells and is normally absent from the surface of even normal CD34+ cells during the first 9 or 10 days in culture.

In the afternoon of experimental "day 0" frozen normal human CD34+ cells (obtained and stored as noted above) were thawed and resuspended in 15 ml of X-VIVO 10 medium supplemented with 1% HSA and the following human recombinant growth factors: (10 μg/ml G-CSF, 100 μg/ml Pixykine [interleukin 3/granulocyte colony stimulating factor {GM-CSF} fusion protein from Immunex Corp], 100 μg/ml flt3-ligand [flt3from Immunex Corp], and 100 μg/ml stem cell factor [SCF from R&D Systems]). This medium is designated in this example and other examples as "standard CD34+ cell medium." The cells with medium were incubated in a standard tissue culture flask overnight in a 37° C. tissue culture incubator at 10% $CO_2$. The next morning (experimental "day 1") CD34+ cells were spun down by low speed centrifugation and suspended in transduction medium consisting of 50% standard CD34+ cell medium and 50% VSN (i.e. MFGS-gp91$^{phox}$ vector supernatant harvested by the 293-SPA packaging line as above) to which was added 6 μg/ml clinical grade protamine. For the portion of the experiment using the 120 ml sized PL2417 flexible containers, 20 ml of the transduction medium with $3.5 \times 10^6$ CD34+ cells was placed in each of two flexible containers (fibronectin fragment CH-296 coated versus uncoated). For comparison 5 ml of the transduction medium with $0.5 \times 10^6$ cells was placed in each of two wells (fibronectin fragment CH-296 coated versus uncoated) of a 6-well standard tissue culture plate.

After 6 hrs of the "day 1" transduction, the contents of the flexible containers or the wells of the plates were removed and the 4 samples individually spun down to recover the cells while discarding the transduction medium. The cells were resuspended in a volume of standard CD34+ cell medium overnight equal to the original volume (5 ml for the well samples and 20 ml for the flexible container samples) and returned to the original culture vessel for an overnight incubation. The next morning the contents of each vessel were removed and centrifuged, the cells resuspended in the same respective volumes of transduction medium, and the cells with transduction medium returned to the respective original culture vessels for the "day 2" transduction of 6 hrs. At the end of the "day 2" transduction, the cells were handled exactly as for "day 1" where they were removed from the transduction medium and resuspended in the original volume of standard CD34+ cell medium for overnight incubation in the respective original vessels. The transduction process was repeated on "day 3" and then the cells were left in standard CD34+ cell medium until analysis on "day 6." All transductions, overnight cultures and subsequent post-transduction culture took place in a 37° C. tissue culture incubator at 10% $CO_2$.

On "day 6" the transduced CD34+ cells were washed and labelled with FITC-conjugated anti-human $gp91^{phox}$ monoclonal antibody. Fluorescence flow cytometric analysis revealed that 82% of the cells in the fibronectin fragment CH-296 coated PL2417 flexible culture container expressed the recombinant $gp91^{phox}$, while only 27% of the cells in the uncoated PL2417 flexible culture container expressed the recombinant $gp91^{phox}$. Thus, because of the inherent uncertainty of conducting transfections in flexible, plastic, gas-permeable culture containers, there was a surprising 3-fold increase in the transduction rate in the fibronectin coated versus uncoated flexible culture container indicating the importance of fibronectin for efficient transduction. Similarly, 86% of cells cultured in the fibronectin fragment coated well of a six well plate expressed the recombinant $gp91^{phox}$ and this represented a more than 2 fold increase of transduction rate compared to that seen with the uncoated well.

Several subsequent studies using the same flexible containers and conditions demonstrated that coating of the PL2417 flexible containers with fibronectin fragment CH-296 consistently resulted in transduction rates that were 3 to 7 fold higher than the results seen in uncoated bags. Similar results of fibronectin fragment enhanced transduction were obtained when the clinically applicable larger 1 liter sized PL2417 flexible containers (17 cm×22.5 cm were studied) were coated with fibronectin fragment. In those laboratory studies the 1 liter sized bag was coated for 2 to 6 hours at room temperature with 40 ml of PBS containing 20 μg/ml fibronectin fragment CH-296 and washed 3 times with 60 ml of PBS containing 1% clinical grade HSA.

With the conditions noted in the detailed experiment above, the inclusion of protamine in the transduction medium surprisingly resulted in maximum transduction. Without inclusion of protamine during the transduction period, the transduction enhancing effect of coating the vessel with fibronectin fragment was markedly reduced. For example, in two experiments with fibronectin coated vessels conducted where conditions were identical to the experiments noted in detail above except for the inclusion or exclusion of 6 μg/ml protamine in the transduction medium transduction rates were 71% with protamine versus 53% without protamine in the first experiment and 90% with protamine versus 16% without protamine in the second experiment. Thus, inclusion of protamine in the liquid phase of the transduction medium unexpectedly demonstrated synergy with the effect of coating the culture vessel with fibronectin fragment CH-296 in enhancing transduction in the PL2417 flexible plastic containers.

EXAMPLE II

Clinical Trial

The following examples demonstrate that patient cells transduced ex vivo in gas-permeable flexible culture containers in the presence of a multi-functional chemical moiety can be used in gene therapy applications.

Since the preclinical studies outlined in Example I indicated that coating of the PL2417 flexible containers with the multi-functional chemical moiety corresponding to the fibronectin fragment CH-296 could greatly enhance retrovirus transduction, the invention method was employed to conduct a clinical trial of gene therapy for the X-linked, $gp91^{phox}$ deficient form of CGD. This clinical trial is currently ongoing and the results of this trial have not been published.

Three patients with the X-linked $gp91^{phox}$ deficient form of CGD were administered 8 daily subcutaneous doses of the marrow growth factors Granulocyte-Macrophage Colony Stimulating Factor 5 μg/kg plus flt3L 50 μg/ml (both growth factors were obtained from Immunex Corp.). On day 8 and 9, the patients underwent an apheresis procedure processing 15 liters on the CS3000 blood cell separator as outlined in Example I. CD34+ cells were separated from the apheresis products using the fully automated ISOLEX 300i immunomagnetic processor (Nexell Therapeutics Inc., Irvine, Calif.) following manufacturer's instructions. The separated CD34+ cells, which averaged 80% to 90% purity and numbered from 150 to 300×$10^6$ cells total from each apheresis preparation, were immediately suspended in about 120 ml of clinical CD34+ cell medium (defined as X-VIVO 10 medium supplemented with 1% HSA and the following human recombinant growth factors: 50 μg/ml Pixykine [Immunex Corp], 100 μg/ml flt3L [Immunex Corp], and 50 μg/ml SCF [R&D Systems]. Thus, the clinical CD34+ cell medium was very similar to the standard CD34+ cell medium described in Example I except for some minor changes in the concentrations of the growth factors and exclusion of G-CSF.

The cells were incubated overnight in a fibronectin fragment CH-296 coated 1 liter size PL2417 flexible plastic container (coating was performed as in the last paragraph of Example I). The next morning a small aliquot of cells was set aside for culture without transduction to serve as a negative control for later analysis of transduction efficiency. For the bulk of the cells, aliquots of 100–200×$10^6$ patient CD34+ cells were centrifuged and re-suspended in about 120 ml of clinical transduction medium prepared similar to that described in Example I except that the ratio of VSN and clinical CD34+ cell medium was 90:10 and the growth factor content of the final clinical transduction medium was identical to that in clinical CD34+ cell transduction medium. Each 120 ml aliquot of cells was placed in a fibronectin fragment CH-296 coated 1 liter sized PL2417 container and incubated for 6–7 hrs to allow transduction to occur. Using this volume in this sized flexible container advantageously results in a fluid layer that is only 3 to 4 mm in depth maximizing interaction of the retrovirus vector and cells with the inner coated surfaces of the PL2417 container. At the end of the transduction, the contents of each bag were removed and pooled, centrifuged and resuspended in an equal volume of clinical CD34+ cell medium. The CD34+ cells derived from the second apheresis from the same patient were then pooled with the cells from the first apheresis that had undergone a single cycle of transduction. The 120 ml each of the pooled cells were returned to the coated PL2417 bags that had been used for the transduction and incubated overnight. The next morning the cells were counted, centrifuged and resuspended in aliquots of 100–200×$10^6$ cells in about 120 ml of clinical transduction medium. Each 120 ml aliquot was placed into a fibronectin fragment CH-296 coated PL2417 flexible plastic container and incubated for 6–7 hrs as with the first day transduction. Except that no additional fresh cells were added to the pool, the process was repeated on a third and fourth day.

At the end of the fourth transduction a small aliquot of the transduced cells was centrifuged, resuspended in standard CD34+ cell medium and set aside for additional culture to allow later analysis of transduction efficiency and assessment of functional correction of neutrophils differentiated in culture from the transduced patient CD34+ stem cells. The bulk of the transduced autologous CD34+ stem cells were washed several times in Plasmalyte A (Baxter, Hyland Division) containing 1% HSA and resuspended into about 50 ml of this fluid in a sterile 60 ml syringe. After safety tests to assure sterility, the cells were administered intravenously to the respective patients.

As in Example I above, transduction efficiency as determined by flow cytometric analysis of surface expression of recombinant gp91$^{phox}$ was determined two to three days after the last transduction. Analysis was preformed on the small aliquots of transduced CD34+ cells that had been set aside in culture from the bulk of the cells that had been administered to the patients as gene therapy treatment. This was compared to the sample of the same patient's cells that had been set aside for culture without undergoing the transduction procedure. A slightly more complex flow cytometric analysis was performed in order assess the efficiency of transduction of the phenotypically more primitive stem cells. It is known that the group of cells that express high levels of surface CD34 antigen and low levels of CD38 antigen contain the bulk of the colony forming cells and primitive stem cells.

By labelling the transduced or non-transduced patient CD34+ cells with antibodies to CD34 antigen, CD38 antigen and gp91$^{phox}$, each with a distinct fluorescent probe it is possible to perform a. "3-color" flow cytometric analysis in which the percent of primitive cells (CD34 bright, CD38 dim) expressing gp91$^{phox}$ protein can be assessed. This analysis is shown in FIG. 3 for patient #1, FIG. 4 for patient #2 and FIG. 5 for patient #3. For each figure four dot plot panels are shown. In each case the left two panels are the non-transduced cells and the right two panels are the clinically prepared transduced cells. In the upper panels the analysis shows the CD38 (vertical axis) and CD34 (horizontal axis expression by these cells). Those cells in the small rectangle seen at the lower right corner of the cluster of cells are those phenotypically primitive cells analyzed for gp91$^{phox}$ protein expression. This analysis of this selected group of primitive cells is shown in the lower panels. The dot plots in the lower panels plot cell size (side scatter) on the vertical axis versus gp91$^{phox}$ expression on the horizontal axis. Cells to the right of the vertical line in the lower panels are defined as gp91$^{phox}$ positive. In the non-transduced population this line is set to allow a background of about 1.2% positivity.

By this analysis, the transduction of cells from patient #1 was 82.9% (after subtracting background); from patient #2 was 80.3%; and from patient #3 was 62.0%. These clinical scale transduction rates are at least about 3 to 5 times higher than that reported in Malech et al. (1997), supra, and also many times higher than any reported experience with transduction of human CD34+ cells in the clinical setting. Furthermore, there was an average 3.5 fold expansion of the CD34+ cells over the 4 days of the clinical scale transduction regimen such that the final harvest of CD34+ cells was from 1 to 2×10$^9$ cells at over 92% viability. In addition the cell products were well tolerated by the patients and passed all FDA mandated safety testing. These data demonstrate that fibronectin fragment CH-296 coated PL2417 flexible plastic containers can be used in the clinical setting of ex vivo gene therapy to achieve extraordinarily high transduction rates of phenotypically primitive stem cells while at the same time fostering proliferation and survival of those cells, and yielding a cellular composition fit for intravenous administration for treatment of patients.

Figure 6A:
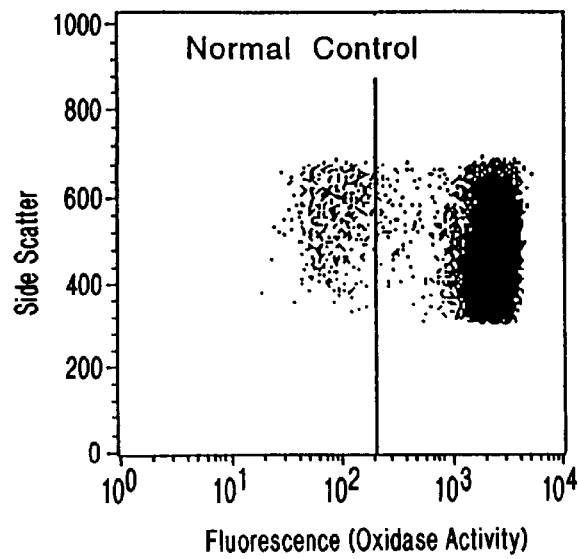
FIG. 6 shows an analysis of hydrogen peroxide production by peripheral blood neutrophils from Patient #2 using a dihydrorhodamine 123 (DHR) flow cytometric assay as described in Example II.
Figure 6B:
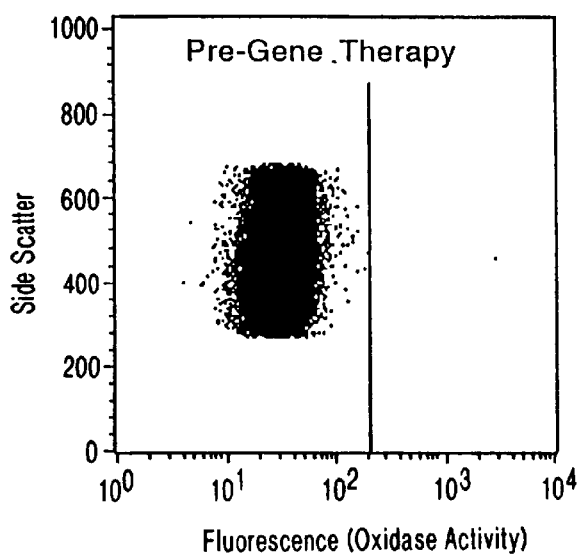
Figure 6C:
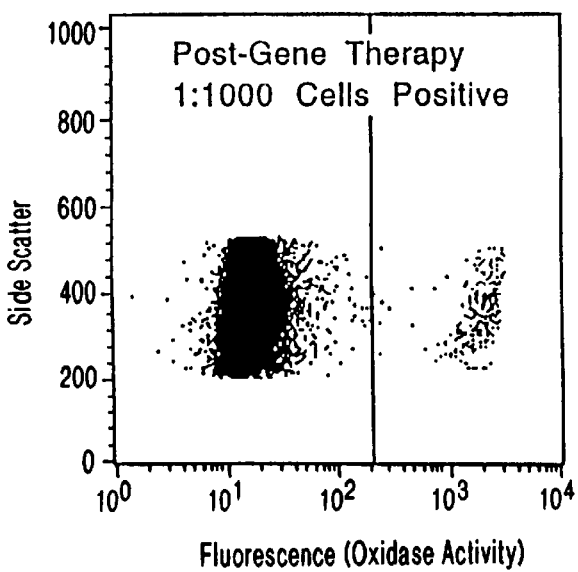

Preliminary results are available indicating engraftment of these transduced cells in the CGD patients. In particular it is shown in FIG. 6 that 25 days after intravenous administration of these transduced cells in Patient #2 functionally normal oxidase positive neutrophils could be detected in the peripheral blood. FIG. 6 is an analysis of hydrogen peroxide production by peripheral blood neutrophils from this patient using a dihydrorhodamine 123 (DHR) flow cytometric assay. The details of this assay have been described or referred in detail in Malech, HL, et al: Proc. Natl. Acad. Sci. USA 94:12133–12138, 1997. In brief, peripheral blood is drawn, the red cells lysed to obtain the blood leukocytes which are then loaded with the DHR ester for 5 minutes. The DHR is de-esterified and thus trapped in the neutrophils. The neutrophils are then stimulated to produce hydrogen peroxide by exposure to phorbol myristate acetate. If oxidants are produced, then the DHR is oxidized with resultant increase in its fluorescence. CGD oxidase negative neutrophils demonstrate low fluorescence while normal oxidase positive neutrophils exhibit high fluorescence in this assay. The appearance of small numbers of high fluorescence neutrophils in a CGD patient following gene therapy is evidence of the production of functionally normal neutrophils which must be derived from gene-corrected CD34+ cells that have engrafted in the patient's bone marrow.

The three panels of FIG. 6 show dot plots in which cells with the size characteristics (side scatter on the vertical axis) of neutrophils are analyzed for oxidant production (DHR fluorescence in the horizontal axis). The top panel shows neutrophils from the peripheral blood of a normal volunteer where almost all the neutrophils are highly fluorescent (e.g., far to the right of the vertical line defining positivity). The middle panel shows this analysis of peripheral blood neutrophils from patient #2 prior to gene therapy where all of the cells show low fluorescence indicating lack of oxidase activity. At 25 days after the administration of the transduced CD34+ cells almost 1 in 1000 of his peripheral blood neutrophil demonstrate high fluorescence equal to normal cells indicating high oxidase activity in these gene therapy corrected neutrophils. Thus, the use of fibronectin fragment CH-296 coated PL2417 bags for enhanced ex vivo transduction of CD34+ cells yielded a cell composition that was capable of engraftment and capable of mediating production of functionally corrected neutrophils into the peripheral blood of a treated patient.

While the invention has been described in detail with reference to certain preferred embodiments thereof, it will be understood that modifications and variations are within the spirit and scope of that which is described and claimed.

---

That which is claimed is:

1. A method of transducing cells comprising:
   providing a flexible closed culture container having cells therein; and
   contacting said cells with a viral-vector in the presence of a multi-functional chemical moiety, wherein said multifunctional chemical moiety comprises a cell-surface binding domain linked to a virus binding domain, said linkage provided by the surface of the flexible closed culture container.

2. The method of claim 1, wherein said cell-surface binding domain is selected from the group consisting of a cell-surface binding fragment of fibronectin, collagen, vitronectin, thrombospondin, and laminin.

3. The method of claim 2, wherein said cell-surface binding fragment of fibronectin is selected from the group consisting of CBD and CS-1.

4. The method of claim 1, wherein said virus binding domain is selected from the group consisting of a virus binding fragment of fibronectin, virus receptors, and antibodies to env gene products.

5. The method of claim 4, wherein said virus binding fragment of fibronectin is heparin binding domain ($III_{12\text{-}14}$).

6. The method of claim 1, wherein said viral-vector is selected from the group consisting of herpes simplex virus, adenovirus, adeno-associated virus, lentivirus, and retrovirus vectors.

7. The method of claim 6, wherein said viral-vector is packaged as a pseudotype virus.

8. The method of claim 6, wherein said viral-vector is a retrovirus vector.

9. The method of claim 8, wherein said retrovirus vector is MFGS.

10. The method of claim 1, wherein said cells are hematopoietic cells.

11. The method of claim 10, wherein said hematopoietic cells are CD34+ stem cells.

12. The method of claim 1, wherein said cells are lymphocytes, dendritic cells, or monocytes.

13. The method of claim 1, wherein said contacting occurs in the presence of a polycation.

14. The method of claim 13, wherein said polycation is protamine.

15. The method of claim 1, wherein said contacting occurs in the absence of serum and animal proteins.

16. A container system for transducing cells, comprising a inflexible closed culture container and a multi-functional chemical moiety therein, wherein said multi-functional chemical moiety comprises a cell-surface binding domain linked to a virus binding domain, said linkage provided by the surface of said flexible closed culture container.

17. The system of claim 16, wherein said cell-surface binding domain is selected from the group consisting of a cell-surface binding fragment of fibronectin, collagen, vitronectin, thrombospondin, and laminin.

18. The system of claim 17, wherein said cell-surface binding fragment of fibronectin is selected from the group consisting of CBD and CS-1.

19. The system of claim 16, wherein said virus binding domain is selected from the group consisting of a virus binding fragment of fibronectin, virus receptors, and antibodies to env gene products.

20. The system of claim 19, wherein said virus binding fragment of fibronectin is heparin binding domain ($III_{12-4}$).

* * * * *